(12) United States Patent
Weinfield

(10) Patent No.: US 12,115,139 B2
(45) Date of Patent: Oct. 15, 2024

(54) TREATMENT METHODS AND PROCESSES FOR AN INFECTED NAIL

(71) Applicant: Todd Alan Weinfield, Redwood City, CA (US)

(72) Inventor: Todd Alan Weinfield, Redwood City, CA (US)

( * ) Notice: Subject to any disclaimer, the term of this patent is extended or adjusted under 35 U.S.C. 154(b) by 0 days.

(21) Appl. No.: 15/998,013

(22) Filed: Aug. 15, 2018

(65) Prior Publication Data

US 2020/0054586 A1 Feb. 20, 2020

(51) Int. Cl.
| | | |
|---|---|---|
| *A61K 31/14* | (2006.01) | |
| *A61K 9/00* | (2006.01) | |
| *A61K 31/095* | (2006.01) | |
| *A61K 31/155* | (2006.01) | |
| *A61K 31/17* | (2006.01) | |
| *A61K 31/45* | (2006.01) | |
| *A61P 31/10* | (2006.01) | |

(52) U.S. Cl.
CPC ............ *A61K 31/14* (2013.01); *A61K 9/0014* (2013.01); *A61K 31/095* (2013.01); *A61K 31/155* (2013.01); *A61K 31/17* (2013.01); *A61K 31/45* (2013.01); *A61P 31/10* (2018.01); *A61K 2300/00* (2013.01)

(58) Field of Classification Search
CPC ...... A61K 31/14; A61K 2300/00; A61P 31/10
See application file for complete search history.

(56) References Cited

U.S. PATENT DOCUMENTS

| | | | |
|---|---|---|---|
| 4,636,520 A | 1/1987 | Umio et al. | |
| 4,957,730 A | 9/1990 | Bohn | |
| 5,002,938 A | 3/1991 | Wang et al. | |
| 5,110,809 A | 5/1992 | Wang et al. | |
| 5,120,530 A | 6/1992 | Ferro | |
| 5,219,877 A | 6/1993 | Shah et al. | |
| 5,264,206 A | 11/1993 | Bohn | |
| 5,346,692 A | 9/1994 | Wohlrab | |
| 5,391,367 A | 2/1995 | DeVincentis et al. | |
| 5,464,610 A | 11/1995 | Hayes, Jr. et al. | |
| 5,487,776 A | 1/1996 | Nimni | |
| 5,652,256 A | 7/1997 | Knowles | |
| 5,696,105 A | 12/1997 | Hackler | |
| 5,795,314 A | 8/1998 | Berenstein | |
| 5,840,283 A * | 11/1998 | Sorenson ................ A61P 17/00 424/405 |
| 5,972,317 A | 10/1999 | Sorenson | |
| 6,143,794 A * | 11/2000 | Chaudhuri ........... A61K 31/137 514/655 |
| 6,231,875 B1 | 5/2001 | Sun | |
| 6,391,879 B1 | 5/2002 | Reeves | |
| 6,465,709 B1 | 10/2002 | Sun et al. | |
| 6,727,401 B1 | 4/2004 | Venkateshwaran et al. | |
| 6,821,508 B2 | 11/2004 | Zatz et al. | |
| 6,921,529 B2 | 7/2005 | Maley | |
| 7,135,194 B2 | 11/2006 | Bimbaum | |
| 8,039,494 B1 | 10/2011 | Winckle | |
| 8,979,820 B2 | 3/2015 | Bailey | |
| 2007/0054834 A1 | 3/2007 | Baker | |
| 2010/0021530 A1 * | 1/2010 | Weinfield .............. A61M 37/00 514/345 |
| 2012/0328543 A1 | 12/2012 | Mallard | |
| 2016/0206567 A1 * | 7/2016 | Ridden ................ A61K 9/0014 |

OTHER PUBLICATIONS

LookChem, Dimethyl di(hydrogenated tallow) ammonium chloride, (accessed May 2, 2019) pp. 1-3 (Year: 2019).*
The Free Dictionary, Applicator, accessed Aug. 3, 2021, pp. 1-3 (Year: 2021).*
Gerald McDonnell and A. Denver Russell Antiseptics and Disinfectants: Activity, Action, and Resistance Clin. Microbiol. Rev. 1999, 12(1):147.
Yoichi Kobayashi , Misao Miyamoto*, Kenji Sugibayashi and Yasunori Morimoto Drug Permeation through the Three Layers of the Human Nail Plate J. Pharm, Pharmacol. 1999, 51: 271±278 # 1999 J. Pharm. Pharmacol. Faculty of Pharmaceutical Sciences, Josai University, 1-1 Keyakidai, Sakado, Saitama 350-0295 and Nissan Chemical Co., Ltd, 3-7-1 Kanda-Nishiki-cho, Chiyoda-ku, Tokyo 101-0054, Japan.
Yoichi Kobayashi A, Tsunehisa Komatsu A, Machiko Sumia, Sachihiko Numajiri, Misao Miyamotob, Daisuke Kobayashi A, Kenji Sugibayashi A, Yasunori Morimoto In vitro permeation of several drugs through the human nail plate: relationship between physicochemical properties and nail permeability of drugs Faculty of Pharmaceutical Sciences, Josai University, 1-1 Keyakidai, Sakado, Saitama 350-0295, Japan.
Priscila Gava Mazzola1, Angela Faustino Jozala2, Leticia Celia De Lencastre Novaes, Patricia Moriel, Thereza Christina Vessoni Penna Minimal inhibitory concentration (MIC) determination of disinfectant and/or sterilizing agents Brazilian Journal of Pharmaceutical Sciences vol. 45, n. 2, abr./Jun., 2009 Department of Clinical Pathology, Faculty of Medical Sciences, State University of Campinas, Department of.
MSDS Baquaspa Sanitizer with Stain & Scale Control Dec. 2, 2009 Arch Chemicals, Inc. 501 Merritt 7 PO Box 5204 Norwalk, CT 06856-5201.

(Continued)

*Primary Examiner* — Andrew S Rosenthal
(74) *Attorney, Agent, or Firm* — My Patent Guys; Christopher Pilling

(57) ABSTRACT

A method of treating nail infections by using keratolytic, quaternary ammonium chloride, biguanide compounds and water heated above nail temperature.

3 Claims, 2 Drawing Sheets

(56) References Cited

OTHER PUBLICATIONS

MSDS Baquaspa Waterline Control Apr. 28, 2009 Arch Chemicals, Inc. 501 Merritt 7 PO Box 5204 Norwalk, CT 06856-5204.

Sudaxshina Murdan Drug delivery to the nail following topical application Department of Pharmaceutics, The School of Pharmacy, University of London, 29-39 Brunswick Square, London WC1N 1AX, UK International Journal of Pharmaceutics 236 (2002) 1-26.

Chad R. Messick, Susan L. Pendland, Majid Moshirfar, Richard G. Fiscella Karen J. Losnedahl, Christopher A. Schriever, and Paul C. Schreckenberger In-vitro activity of polyhexamethylene biguanide (PHMB) against fungal isolates associated with infective keratitis J Amtimicrob Chemother 1999: 44: 297-298 Ophthalmology and Pathology, University of Illinois Chicago, IL; John A. Moran Eye Center, Salt Lake City, UT, USA.

Vantocil FHC Antimicrobial 2009 Product Information Bulletin Arch Biocides 5660 New Northside Drive, Suite 1100, Atlanta, GA 30328.

David Quintanar-Guerrero, Adriana Ganem Quintanar, Patricia Tapia-Olguin, Yogeshvar N.Kalia and Pierre Buri The Effect of Keratolytic Agents on the Permeability of Three Imidazole Antimycotic Drugs Through the Human Nail Drug Development and Industrial Pharmacy, 24(7), 685-690 (1998) FES-Cuautitlan, Universidad Nacional Autonoma de Mexico, Mexico City.

GPS Product Safety Summary Clariant Procukte (Deutschland) GMbH Product No. GPSSR-78 Quaternary ammonijum compounds, bis(hydrogenated tallow alkyl) dimethyl, chlorides 65926 Frankfurt am Main +49 69 305 18000.

Gopal Rathore, Abhad Doshi Nail Drug Delivery System: A Review International Journal of universal Pharmacy and Bio Sciences 3(5): Sep.-Oct. 2014 (ISDN): 2319-8141.

Betrand Favre, Bettina Hofbauer, Kwang-Soo Hildering, Neil S. Ryder Comparison of In Vitro Activities of 17 Antifungal Drugs against a Panel of 20 Dermatophytes by Using a Microdilution Assay Journal of Clinical Microbiology Oct. 2003 p. 4817-4819 Novartis Research Institute Vienna, Austria.

Timby, Barbara Kuhn. Essentials of Nursing: Care of Adults and Children 2005 Lippincott Williams & Wilkins Philadelphia 2005 p. 928.

Krasaeath, Rebecca et al Topical Antifungals for Treatment of Onychomycosis. American Family Physician vol. 94 No. 9 2016.

Baran R et al Topical antifungal drugs for the treatment of onychomycosis; an overview of current strategies for monotherapy and combination therapy European Academy of Dermatology and Venereology 2005 19, 21-29.

Gilliver, Stephen PHMB: a well-tolerated antiseptic with no reported toxic effects Journal of Would Care / Activa Healthcare Supplement 2009.

CDC Guideline for Disinfection and Sterilization in Healthcare Facilities, 2009 Updated 2019 p. 52-53.

Askeland, Donald The Science and Engineering of Materials Wadsworth, Inc. Belmont 1984 p. 95-97.

Product Insert Ciclopirox Olamine—ciclopirox olamine suspension Padagis Israel Pharmaceuticals Ltd Sep. 2021 https://dailymed.nlm.nih.gov/dailymed/lookup.cfm?setid=eadbd29d-5990-4987-833f-40cd0b2d2868.

Shen et al Repositioning the Old Fungicide Ciclopirox for New Medical Uses Curr Pharm Des. 2016 : 22(28): 4443-4450.

Gutchup et al Structural characteristics and permeability properties of the human nail: A review J. Cosmet.Sci., 59, 363-385 (Nov. / Dec. 1999).

Creppy et al Study of Epigenetic Properties of Poly(HexaMethylene Biguanide) Hydrochloride (PHMB) Int. J. Environ. Res. Public Health 2014, 11, 8069-8092.

* cited by examiner

Example 1 FIG. 1
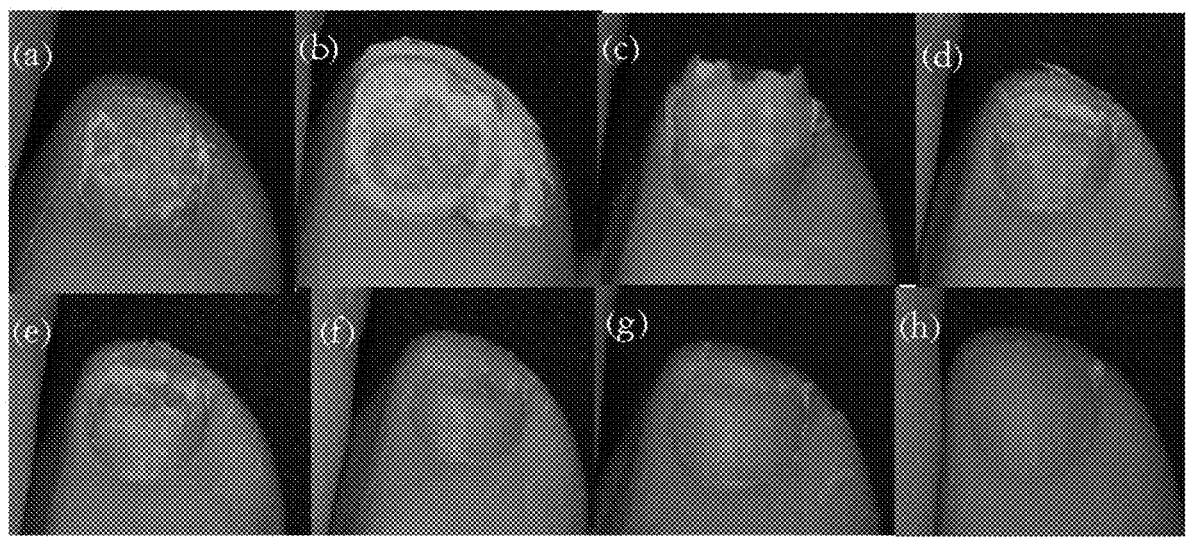

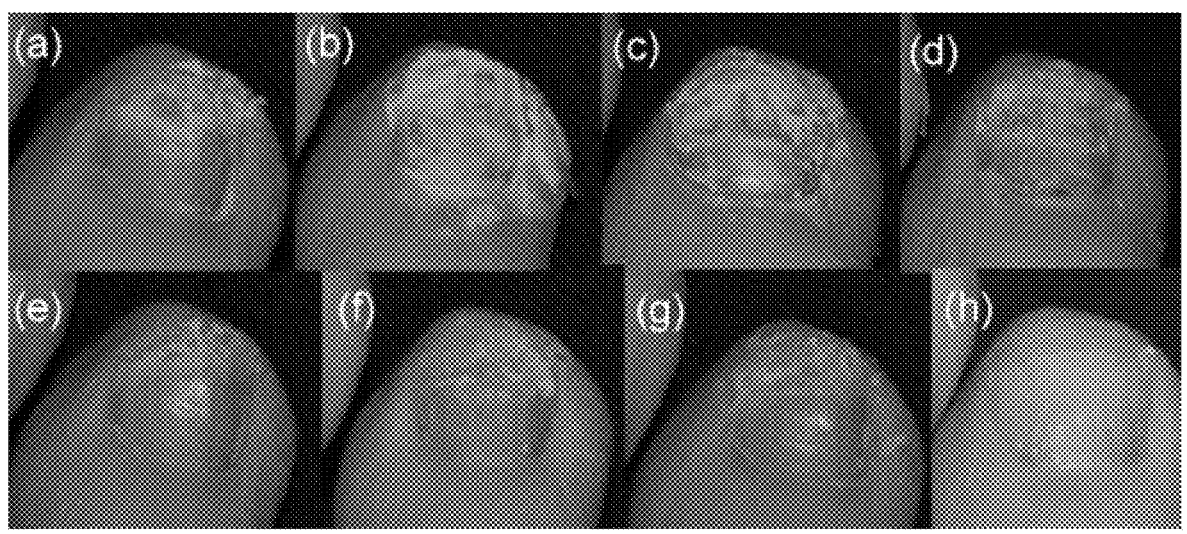
Example 2 FIG. 2

TREATMENT METHODS AND PROCESSES FOR AN INFECTED NAIL

CROSS REFERENCE TO OTHER APPLICATIONS

This application claims the benefit of provisional patent application 62/604,654 filed on Jul. 15, 2017 entitled Nail Infection Treatment Apparatus, Methods, Mechanisms, Modes of Action and Processes.

FEDERALLY SPONSORED RESEARCH OR DEVELOPMENT

None.

BACKGROUND OF THE INVENTION

Field of the Invention

The teachings provided herein are directed to methods and compositions that facilitate the delivery of therapeutic composition(s) through the nail of a subject having a nail infection.

Prior Art

The development of a cure for nail infections has historically focused on solving only one problem—delivering known medication (developed to treat skin infections) through the infected nail to treat the condition. Approximately 10% of the U.S. population under the age of 70 is infected with the condition, but that figure increases to 48% for those over 70. The infection is especially risky for diabetics. If uncontrolled, diabetics risk limb amputation. One third of the world's nearly 400 million diabetics have nail infections.

Current approaches have yielded only marginal results with cure rates for the best treatments under 40% only for surface or mild infections not involving the nail bed. Clearly, a more effective approach is needed.

The nail provides a seemingly impenetrable membrane protecting the infection from outside elements as Quintanar-Guerrero et al from Universidad Nacional Autonoma de Mexico have shown n in their paper The effect of keratolytic agents on the permeability of three imidazole antimicrobial drugs through the human nail (Drug Dev Ind Pharm, Jul. 1, 1998; 24(7): 685-90).

Quintanar-Guerrero et al also found that keratolytic substances such as papain. and salicylic acid used in combination did enhance the permeability of the antimicrobial. Patents with methods, formulae, and apparatus to increase the permeability of the antimicrobial through the nail into the nail bed dominate this art See, for example, the following U.S. patents and patent application publications: U.S. Pat. Nos. 6,821,508; 6,921,529; 5,795,314; 6,727,401; 6,465,709.

The prior art also includes many topical therapies for the treatment of nail disorders. Bohn in U.S. Pat. No. 4,957,730, describes a nail varnish containing a water-insoluble film-forming substance and antimicrobial compound. Ferro in U.S. Pat. No. 5,120,530, teaches an antimicrobial nail varnish containing amorolfine in quaternary ammonium acrylic copolymer. Bohn in U.S. Pat. No. 5,264,206, describes a nail lacquer with antimicrobial activity which contains an antimicrobial agent and water-insoluble film formers including polyvinyl acetate.

Wohlrab in U.S. Pat. No. 5,346,692, describes a nail lacquer for treating nail infections, comprised of a film-forming agent, an antimycrobially active substance, and urea. Nimni in U.S. Pat. No. 5,487,776, describes a nail lacquer composition which forms a water permeable film containing griseofulvin. Chaudhuri in U.S. Pat. No. 6,143,794, describes a topical formulation for the treatment of nail infections that includes a solvent, gelling agent, adhesion-promoting agent, a film-forming agent, a surfactant, and optionally a keratolytic agent.

Knowles in U.S. Pat. No. 5,652,256, describes the use of methyl acetate as a penetration enhancing compound in combination with naftifine or sulconazole and naftifine as a topical gel for treatment of nail infections. Sorenson in U.S. Pat. No. 5,972,317, discloses that a proteolytic enzyme such as papain that is delivered by pads soaked in the enzyme solution and produces a more permeable nail. Sun in U.S. Pat. No. 6,231,875, teaches acidified compositions of antimicrobials to enhance transport across nails and skin. Reeves in U.S. Pat. No. 6,391,879 describes the combination of an antimicrobial agent in an anhydrous blend of polyglycol and DMSO.

Birnbaum in U.S. Pat. No. 7,135,194, discloses a subunguicide with an antimicrobial agent administered between the hyponychium and the nail plate. Winckle in U.S. Pat. No. 8,039,494 teaches a composition containing a triazole antimicrobial pharmaceutically active agent, a solvent, and a wetting agent in a composition which does not form a solid film when applied to the surface of a nail. Bailey in U.S. Pat. No. 8,979,820 teaches a sequence of steps how to improve the appearance of infected nails that includes soaking them in camphor and boric acid. Baker in US 2007/0054834 describes using quaternary ammonium halides to treat infectious conditions on skin. Mallard et al in US 2012/0328543 teaches using surfactants to facilitate the delivery of antimicrobial agents into the infected nail.

Other U.S. Patents that teach combination antimicrobial products include, for example: U.S. Pat. No. 4,636,520 (combination of imidazole and pyrrolnitrin); U.S. Pat. No. 5,002,938 (gel combination of imidazole and 17-ester corticosteroid anti inflammatory agent); U.S. Pat. No. 5,110,809 (antimicrobial gel plus steroid); U.S. Pat. No. 5,219,877 (gel product with imidazole antimicrobial optionally with steroidal anti-inflammatory in a vehicle system that includes lauryl alcohol); U.S. Pat. No. 5,391,367 (aqueous alcoholic gel with tioconazole); U.S. Pat. No. 5,464,610 (salicylic acid plaster); and U.S. Pat. No. 5,696,105 (mometasone furoate).

Existing or protocols in development for treating nail infections fit into one of four categories: 1) oral or systemic; 2) topical; 3) light, electromagnetic or gas plasma; 4) iontophoresis or electrophoresis.

1) Oral treatments include Griseofulvin, Ketoconazole, Lamisil, Sporanox, Posaconazole, and Albaconazole (a typical 12 month course costs between $1,350 and $2,700). Lamisil has been the most effective with a mycological cure rate of 46%. The limited success of Lamisil in the market is attributed to its potential for toxic side effects, high relapse rate, long treatment times, marginal cure rates, and the tendency of the infection to inhabit portions of the nail which are not vascularized. Posaconazole and Albaconazole post similar results but are prone to fewer side effects than Lamisil.

2) Topical treatments include: amorolfine, ciclopirox, efinaconazole, tavaborole, and luliconazole. Amorolfine (Galderma) does not have FDA approval is not available in the United States, however, has shown cure rates of 40 to 55% for mild nail infections without nail matrix involvement, however, it is not effective against severe nail infections involving the nail bed. A typical course of amorolfine is 12 months and costs $1,080. Ciclopirox is the only FDA approved medication for the condition and has cure rate for the 8% strength of about 8.5%.

Valeant's efinaconazole demonstrated cure rates of 17.8% and 15.2% only for mild infections not involving the nail bed. Analysts estimate peak annual sales of efinaconazole at $200 million. Anacor's Tavaborole (boron-based) achieved complete cure in 6% of the 600 patients in the study. Other topical treatments of less interest include: Cindacin (DSMO and tolnaftate from Pedicis Research); Emtrix, Nalox, and Kerasal Nail (urea, propylene glycol and lactic acid from Paladin Labs) are used to treat symptoms of nail infections or psoriasis including discolored or brittle nails, but not treat the condition itself.

3) Light, electromagnetic and gas plasma Companies such as Keraderm, Patholase, Nomir, and Devicefarm have developed light energy and gas plasma technology to treat infections taking advantage of UV, laser light and chlorine gas plasma's ability to inhibit the growth of the infection in vitro. The build up of keratin debris under the nail plate prevents light and plasma from penetrating the nail. The best published effective rate for light energy is Patholase with a 10% cure rate (placebo is 6%) administered during an office visit for $900-$1,200 per application.

Devicefarm gas plasma ($1,500 to $2,000 for three office visits) has not published the results from their clinical trials despite evidence that skin infections require more than three treatments to cure, the concentration of chlorine necessary to effectively treat dermatophyties is toxic to human skin and the plasma fails to completely penetrate even half the thickness of a normal nail.

Dusa Pharmaceuticals patented photodynamic therapy in which a therapeutic agent is applied to the nail several days prior to exposing the nail to light that causes an activation reaction. The published data for photodynamic therapy since 2008 suggests it improves the appearance of infected nails but is unable to penetrate deep enough to effectively treat the infection.

4) Iontophoresis, electrophoresis and implant Startup NB Therapeutics (Nitric Biotherapeutics) developed an iontophoretic process that transports terbinafine hydrochloride (Lamisil) through the nail. Unfortunately, the results of the clinical trials were unable to convince investors to continue pursuing this approach so the company failed. Lamisil implant startup Hallux (formerly Talima) has only started recruiting for clinical trials.

None of these methods have been shown to be consistently clinically effective in treating nail infections. For this reason, a successful, safe, and noninvasive topical treatment for nail infections is a long-felt and unsolved need which is well-understood and accepted by those skilled in the art.

Accordingly, those skilled in the art of treating nail infections, and the patients suffering such nail infections, will appreciate a successful, safe, and non-invasive topical treatment for nail infections. The present teachings provide such a method of treatment that (i) is topical and safe; (ii) does not require oral or systemic administration of drugs; (iii) is safer for patients that may be intolerant to systemic drug delivery; (iv) is several times faster than existing topical treatments; (v) does not require removal of the nail; and, as such, (vi) does not require the patient to do without the presence of a nail for the year or so required to grow a new nail. These are examples of the advantages that will be realized in the art by the teachings provided herein.

BRIEF SUMMARY OF THE INVENTION

Whereas treating infected nails with keratolytic and antimicrobial ingredients is known in this art, new to this art and discovered unexpectedly is the selection and application of keratolytic and antimicrobial ingredients in warm water that optimizes cure rates and convenience but minimizes treatment time and patient risk. To that end and new to this art is the scientific breakdown and understanding of the individual challenges in treating nail infections which, when assembled into a single targeted approach, effectively treats the condition in vivo regardless of severity, etiology or age of the infection. Below is that breakdown.

A first aspect for these embodiments is nail hydrophilicity. Known in this art is that nail keratin is hydrophilic (absorbs water). New to this art is the discovery that nail keratin will also absorb larger molecules (>18 g/mol) and deliver them with their modes of action intact through the nail to effectively treat infections.

A second aspect for these embodiments is energy from heat. Known in this art is that energy (heat) is required for water molecules to penetrate nail keratin to reach the infection (why nails become soft in warm water and harden in cold water). New to this art is the discovery that heat energy drives higher molecular weight antimicrobials (>18 g/mol) through nail keratin to effectively treat infections at temperatures greater than recommended without denaturing them.

A third aspect for these embodiments is nail thickness. Known in this art is that keratolytic compounds applied to nail keratin reduce the thickness of the nail and keratin debris (infection waste product) and enhance the permeability of the antimicrobial. New to this art is the application of keratolytic compounds that allows larger more potent antimicrobials to penetrate the nail to effectively treat the infection.

A fourth aspect for these embodiments is electrostatic repulsion. Known in this art is the electrostatic build up between the antimicrobial and the nail that prevents the antimicrobial from penetrating. New to this art and discovered unexpectedly is that quaternary ammonium chlorides facilitate this delivery in addition to adding modes of action to treat the infection where non-ionic, anionic, amphoteric, sufactatergent and emulsifiers are less effective.

A fifth aspect for these embodiments is antimicrobial potency. Known in this art to treat nail infections is the application of established medications to the nail. Traditional antimicrobials usually exhibit no more than one or two modes of action to treat the condition which allows the infection to build up resistance to the medication. New to this art is the delivery of larger antimicrobial molecules (with antimicrobial potency inferred from antibacterial studies) that inhibits infection resistance by disabling many cellular functions simultaneously.

A sixth aspect for these embodiments is molecular weight and orientation. Known in this art is that smaller molecular weight antimicrobials are able to accumulate in higher concentrations under the nail because of their smaller size. New to this art is the discovery of the delivery of higher molecular weight antimicrobials that accumulate under the nail in high enough concentrations to effectively treat the infection despite their larger size. Driving this delivery is the discovery of antimicrobials with molecular orientation that align with the nail plate structure to allow penetration.

DRAWINGS

Example 1 FIG. 1 shows the successful treatment of an infected nail (with Trichophyton Rubrum and or Trichophyton Mentagrophytes) pretreated with 30% salicylic acid once daily. Following pretreatment, the infected nail was soaked in a mixture of 0.10% bis (hydrogenated tallow alkyl) dimethyl quaternary chlorides and 0.15% poly (hexamethylenebiguanide) hydrochloride in water and heated above nail temperature (approximately 40° C.) for 10 to 15 minutes daily during the treatment period.

Example 2 FIG. 2 shows the successful treatment of an infected nail (with Trichophyton Rubrum and or Trichophyton Mentagrophytes) that was periodically trimmed during the 90 day treatment period. After trimming, the infected nail was soaked in a mixture of 30% salicylic acid, 0.10% bis (hydrogenated tallow alkyl) dimethyl quaternary chlorides and 0.15% poly (hexamethylenebiguanide) hydrochloride in water and heated above nail temperature (approximately 40° C.) for 10 to 15 minutes daily during the treatment period.

DETAILED DESCRIPTION OF THE INVENTION

The following description of the invention will typically be with reference to embodiments and methods. It is to be appreciated that there is no intention to limit the invention to the specifically disclosed embodiments and methods but that the invention may be practiced using other features, elements, methods and embodiments not to limit its scope, which is defined by the claims. Those of ordinary skill in the art will recognize a variety of equivalent variations on the description that follows.

Keratolytic compositions that disrupt protein structure are typically used in treating acne and warts on skin. Keratolytic compositions are well known and available from commercial laboratories such as Santa Cruz Biotechnology (SC) and Sigma Aldrich (SA). Keratolytic agents include but are not limited to: lactic acid (SC-215227), allantoin (SA-05670), zinc pyrithione (SC-229790), sulfur (SC-215933, rosorcinol (SC-203371), undecylenic acid (SC-296681), papain (SA P4762), salicylic acid (SC-203374), urea (SC-29114), magnesium sulfate (SC-250284), aminomethylpropanol (SC-209002), hydroxyalkylphosphonate (SA-777161), pancreatin (SA P-7545), subtilisin (SA P5380), retinol (SC-210706 & SA R7632), benzoyl peroxide (SC-214588), azelaic acid (SC-257106), trypsin (SC-391055) or combinations thereof.

Keratolytic compounds in safe concentrations ranges from 30% to 50% (applied separately or together) may be applied to the infected nail(s) separately once per day for up to 90 days or included with the antimicrobial solution and heated for soaking the infected nail(s).

Quaternary ammonium chlorides are antimicrobial cationic surfactants that reduce surface tension and include antimicrobial modes of action. Quaternary ammonium chlorides are typically used as surface disinfectants.

Quaternary ammonium chlorides are well known and are commercially available: alkoxylated alkano lamides such as Makon® NF-5 (Stepan Co., Northfield, M.); di(hydrogenated tallow alkyl)-dimethyl quaternary ammonium chlorides such as Arquad@ 2HT-75 (Akzo Chemicals Inc., Chicago, IL); tallow alkyl benzyl dimethyl quaternary ammonium chloride such as Kemamine BQ-9742C (Witco Chemical Corp., Memphis, Tenn.) and hydrogenated tallow alkyl benzyl dimethyl quaternary ammonium chloride such as Kemamine Q-9702C (Witco Chemical Corp.), Bis (hydrogenated tallow alkyl) dimethyl quaternary chlorides from Lonza part number 904578, methyl bis(soya alkyl amidoethyl) 2-hydroxyethyl quaternary ammonium methyl sulfate such as Accosoft 750 (Stepan Co. Northfield, IL); methyl bis(tallow alkyl amidoethyl) 2-hydroxyethyl quaternary ammonium methyl sulfate such as Accosoft 501 (Stepan Co.).

Quaternary ammonium chlorides in safe concentrations less than 0.3% are heated above nail temperature and penetrate the infected nail with water. Biguanides are well known antimicrobials typically used as public water treatments and surface disinfectants. Biguanides include but are not limited to and are commercially available: Polyhexamethylene biguanide; polyhexamethylene guanide; poly(iminoimidocarbonyliminoimido carbonylimino hexamethylene); poly(hexamethylenebiguanide); polyaminopropyl biguanide (PAPB), polihexanide (PHMB) from Lonza (Switzerland); dibrompropamidine (Brolene—Aventis Pharma), Golden Eye (Typharm Ltd); hexamidine (Aurigoutte—Merck & Cyteal—Pierre Fabre); alexidine (Cayman Chemical); and chlorhexidine (3M, King).

Biguanides in safe concentrations less than 0.3% are heated above nail temperature and penetrate infected nail(s) with water.

One or more quaternary ammonium chloride (concentration in water less than 0.3%) and/or one or more biguanide compound (concentration in water less than 0.3%) are mixed with water and together are absorbed into the infected nail(s). Keratolytic ingredients may be applied separately to infected nail(s) (concentration less than 30%) or included with the quaternary ammonium chloride and biguanide compounds with water (concentration less than 50%).

The mixture is heated above nail temperature (usually 5°-10° C. less than body temperature of 37° C. and less than the FDA maximum of 45° C.). Heat energy helps mixture overcome the infected nail's natural resistance to absorption (why nails soften in warm water and harden in cold water).

Embodiments may include one or more keratolytic ingredient, one or more quaternary ammonium compound ingredient and water heated above nail temperature. Other embodiments may include one or more keratolytic ingredient, one or more biguanide ingredient and water heated above nail temperature. Further embodiments may include one or more keratolytic ingredient, one or more quaternary ammonium compound ingredient, one or more biguanide ingredient and water heated above nail temperature.

Safe therapeutically effective concentrations of keratolytic ingredients for all embodiments is less than 50%; for quaternary ammonium chloride ingredients is less than 0.3%; and for biguanide ingredients less than 0.3%. Temperature range for all embodiments is above nail temperature (usually 5°-10° C. less than body temperature of 37° C. and less than the FDA maximum of 45° C.).

Treatment duration depends on the severity of the infection and ranges from soaking infected nails in warm antimicrobial solution from 5 to 15 minutes once per day for 20 to 120 days.

The treatment of an infected nail requires administering an agent to a subject having an infected nail. The terms "administration" or "administering" refer to a method of incorporating a composition into the cells or tissues of a subject, either in vivo or ex vivo to diagnose, prevent, treat, or ameliorate a symptom of a disease. In one example, a compound can be administered directly to the affected tissue of a subject. In another example, a compound can be administered to a subject by combining the compound with cell tissue from the subject ex vivo for purposes that include, but are not limited to, assays for determining utility and efficacy of a composition. When the compound is incorporated on the subject in combination with one or active agents, the terms "administration" or "administering" can include sequential or incorporation concurrent incorporation of the compound with the other agents such as, for example, any agent described above. A pharmaceutical composition of the embodiment is formulated to be compatible with its intended route of administration.

An "effective amount" of a compound of the embodiment can be used to describe a therapeutically effective amount or a prophylactically effective amount. An effective amount can also be an amount that ameliorates the symptoms of a disease. A "therapeutically effective amount" refers to an amount that is effective at the dosages and periods of time necessary to achieve a desired therapeutic result and may also refer to an amount of an active compound, drug or pharmaceutical agent that elicits any biological or medicinal response in a tissue, system, or subject that is sought by a researcher, veterinarian, medical doctor or other clinician that may be part of a treatment plan leading to a desired effect.

The term "treating" refers to the administering one or more therapeutic or prophylactic agents taught herein. A "prophylactically effective amount" refers to an amount that is effective at the dosages and periods of time necessary to achieve a desired prophylactic result such as, preventing or inhibiting the severity of condition. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, the therapeutically effective amount may need to be administered in an amount sufficient to result in amelioration of one or more symptoms of a disorder, prevention of the advancement of a disorder, or regression of a disorder. In one example, a therapeutically effective amount preferably refers to the amount of a therapeutic mechanism that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the mode of action.

EXAMPLES

Example 1

A subject having a nail infection diagnosis of a Trichophyton genus was treated using a variety of the methods taught herein. The presence of hyphae in the subject was consistent with Trichophyton Rubrum and or Trichophyton Mentagrophytes (the diagnosis of mixed infections is difficult to determine accurately). Nails infected with these organisms also produce a chronic type of tinea pedis. Infections involving the interdigital areas can produce erythema, fissuring, and may extend into other portions of the hand or foot.

In this example, the infected nail was periodically trimmed during the 90 day treatment period and pretreated with 30% salicylic acid once daily. Following pretreatment, the infected nail was soaked in a mixture of 0.10% bis (hydrogenated tallow alkyl) dimethyl quaternary chlorides and 0.15% poly(hexamethylenebiguanide) hydrochloride in water and heated above nail temperature (approximately 40° C.) for 10 to 15 minutes daily during the treatment period.

Example 2

A subject having a nail infection diagnosis of a Trichophyton genus was treated using a variety of the methods taught herein. The presence of hyphae in the subject was consistent with Trichophyton Rubrum and or Trichophyton Mentagrophytes (the diagnosis of mixed infections is difficult to determine accurately). Nails infected with these organisms also produce a chronic type of tinea pedis. Infections involving the interdigital areas can produce erythema, fissuring, and may extend into other portions of the hand or foot.

In this example, the infected nail was periodically trimmed during the 90 day treatment period. After trimming, the infected nail was soaked in a mixture of 30% salicylic acid, 0.10% bis (hydrogenated tallow alkyl) dimethyl quaternary chlorides and 0.15% poly(hexamethylenebiguanide) hydrochloride in water and heated above nail temperature (approximately 40° C.) for 10 to 15 minutes daily during the treatment period.

Examples 1 and 2 show the successful treatment of an infected nail using the teachings described herein. As can be seen from the figures, this treatment eliminates the infection and provides clinical cure.

What is claimed is:

1. A method that enables higher molecular weight antimicrobials (>18 g/mol) to pass through and accumulate under nail keratin in an effective concentration for treatment of an infection of a nail or nail bed of an individual suffering from said infection, wherein the infection is treated by soaking infected nail(s) in an effective concentration (<0.3%) of a bis (hydrogenated tallow alkyl) dimethyl quaternary chlorides and (<0.3%) poly (hexamethylenebiguanide) hydrochloride solution;
wherein said solution is mixed with water and heated above nail temperatures, and salicylic acid is administered.

2. The method of claim 1 wherein infected nail is pretreated with said salicylic acid.

3. The method of claim 1 wherein said salicylic acid is combined with said bis (hydrogenated tallow alkyl) dimethyl quaternary chlorides and poly (hexamethylenebiguanide) hydrochloride solution.

* * * * *